(12) United States Patent
Koh et al.

(10) Patent No.: US 9,994,627 B2
(45) Date of Patent: Jun. 12, 2018

(54) METHODS FOR PURIFYING ERYTHROPOIETIN ANALOGS HAVING LOWER ISOELECTRIC POINT

(71) Applicant: CHONG KUN DANG PHARMACEUTICAL CORP., Seoul (KR)

(72) Inventors: Yeo-Wook Koh, Yongin-Si (KR); Sang-Yong Lee, Yongin-Si (KR); Cook-Hee Kim, Yongin-Si (KR); Seung-Hui Lee, Yongin-Si (KR); Ha-Na Kim, Yongin-Si (KR); Su-Yon Kim, Yongin-Si (KR); Jin-Hyun Seong, Yongin-Si (KR); Yong-Hyun Cho, Yongin-Si (KR)

(73) Assignee: CHONG KUN DANG PHARMACEUTICAL CORP., Seoul (KR)

( * ) Notice: Subject to any disclaimer, the term of this patent is extended or adjusted under 35 U.S.C. 154(b) by 51 days.

(21) Appl. No.: 14/352,734

(22) PCT Filed: Sep. 28, 2012

(86) PCT No.: PCT/KR2012/007959
§ 371 (c)(1),
(2) Date: Apr. 18, 2014

(87) PCT Pub. No.: WO2013/058485
PCT Pub. Date: Apr. 25, 2013

(65) Prior Publication Data
US 2014/0243510 A1   Aug. 28, 2014

(30) Foreign Application Priority Data
Oct. 18, 2011   (KR) .................. 10-2011-0106230

(51) Int. Cl.
*C07K 14/505*   (2006.01)
*C07K 1/14*   (2006.01)
*C07K 1/16*   (2006.01)
*C12N 5/00*   (2006.01)
*C12N 15/00*   (2006.01)

(52) U.S. Cl.
CPC ............. *C07K 14/505* (2013.01); *C07K 1/14* (2013.01); *C07K 1/16* (2013.01); *C12N 5/00* (2013.01); *C12N 15/00* (2013.01)

(58) Field of Classification Search
None
See application file for complete search history.

(56) References Cited

U.S. PATENT DOCUMENTS

| 5,856,298 | A | 1/1999 | Strickland |
| 7,012,130 | B1 | 3/2006 | Carcagno et al. |
| 2007/0293420 | A1* | 12/2007 | Schumann et al. ............... 514/8 |
| 2009/0029907 | A1 | 1/2009 | Patell |
| 2011/0098452 | A1 | 4/2011 | Roy et al. |
| 2011/0190194 | A1* | 8/2011 | Lim ..................... C07K 14/811 514/1.4 |
| 2012/0264688 | A1* | 10/2012 | Hinderer .............. C07K 14/505 514/7.7 |

FOREIGN PATENT DOCUMENTS

| EP | 0148605 A2 | 7/1985 |
| EP | 1 428 878 A1 * | 6/2004 |

OTHER PUBLICATIONS

International Search Report for International Application No. PCT/KR2012/007959, dated Mar. 18, 2013 (4 pages).

* cited by examiner

*Primary Examiner* — Joanne Hama
*Assistant Examiner* — Regina M DeBerry
(74) *Attorney, Agent, or Firm* — Clark & Elbing LLP; Susan M. Michand

(57) ABSTRACT

The present invention relates to a method for purifying an erythropoietin analog having a low isoelectric point below 4 by adding an N-linked sugar chain with high purity. In accordance with the present invention, the erythropoietin analog having an isoelectric point below 4, which is an isoform having more sialic acid residues, can be effectively purified via three-step chromatographic processes in short time at lower cost.

8 Claims, 12 Drawing Sheets

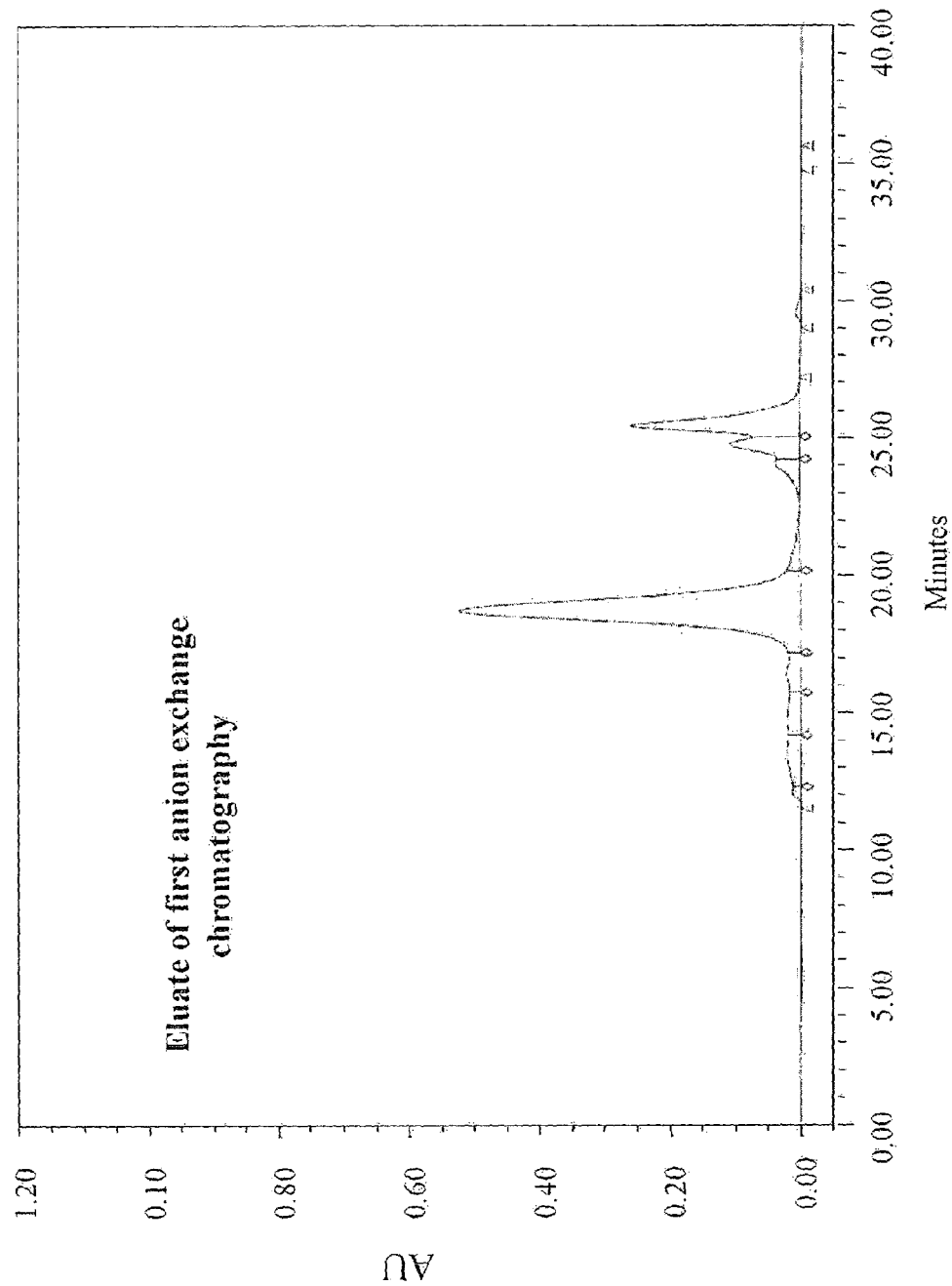

METHODS FOR PURIFYING ERYTHROPOIETIN ANALOGS HAVING LOWER ISOELECTRIC POINT

CROSS-REFERENCE TO RELATED APPLICATIONS

This application is the U.S. national stage filing under 35 U.S.C. § 371 of international application PCT/KR2012/007959, filed Sep. 28, 2012, which claims priority from KR Patent Application No. 10-2011-0106230, filed Oct. 18, 2011.

BACKGROUND OF THE INVENTION

Technical Field

The present invention relates to a method for purifying an erythropoietin analog having a low isoelectric point below 4 by adding an N-linked sugar chain with high purity.

Background Art

Erythropoietin is an erythropoiesis-stimulating factor that promotes red blood cell production by stimulating hematopoietic stem cells and facilitating their differentiation into erythrocytes. Erythropoietin (or EPO) is a glycoprotein having three N-linked sugar chains and one O-linked sugar chain and is used to treat anemia in patients with chronic kidney disease, cancer and the like. The number of sialic acid residues in the sugar chains of EPO affects the half-life and biological activity of EPO in blood. An isoform having a larger number of sialic acid residues has higher biological activity as degradation of EPO is suppressed (Egrie J C. and Browne J K., *Br. J. Cancer,* 2001; 84, 3-10 and Egrie et al., *Glycoconj. J.,* 1993; 10: 263-269).

Recently, a novel erythropoiesis-stimulating protein (NESP), which is an erythropoietin analog with a low isoelectric point obtained by adding N-linked sugar chains to naturally occurring erythropoietin through genetic modification in order to increase biological activity, has been produced. Darbepoetin alfa is an NESP currently available as drug (Egrie and Browne, *Br. J. Cancer.* 84 Suppl. 1, 3-10 (2001)). NESP is a glycoprotein consisting of 165 amino acids. Whereas naturally occurring EPO has up to 14 sialic acid residues, NESP has up to 18 or 22 sialic acid residues by added N-linked sugar chains. Sialic acid is a sugar acid. As the number of sialic acid residues increases as a result of addition of the N-linked sugar chains, whereby the NESP molecule has a lower isoelectric point (pI) (Rush R S, et al., *Anal. Chem.,* 1995; 67: 1441-52).

Since the NESP obtained by addition of the sialic acid residues has 3 times longer half-life in serum as compared to the existing recombinant erythropoietin, equivalent therapeutic effect can be expected with fewer administrations when treating anemia of patients with chronic kidney disease. The sialic acid content of EPO is directly related with the drug release duration in vivo and thus is regarded as an important property of the glycoprotein. The sialic acid residue at the terminal of the sugar chain of EPO protects the second galactose residue of the sugar chain, thereby inhibiting the degradation of the galactose residue by the hepatocyte receptor, extending half-life of EPO in vivo and improving its biological activity (Goldwasser et al, *J. Biol. Chem.* 249, 4202-4206 (1974), Lowy et al., *Nature.* 185, 102-103 (1960)).

A method of producing EPO using animal cells is disclosed in the following patent. Korean Patent Registration No. 10-0423615 describes a method for producing erythropoietin by culturing EPO-producing cells on a serum-free flask or roller and purifying them sequentially by Blue Sepharose adsorption chromatography, hydrophobic chromatography, anion exchange chromatography and high-speed liquid chromatography. However, this patent does not describe a method for producing NESP, and the purification procedure involving the four chromatographic processes disclosed in the patent is complicated.

In addition, use of immunoadsorption chromatography is described in Korean Patent Registration Nos. 10-0153808 and 10-0900013, use of dye affinity chromatography is described in Korean Patent Registration Nos. 10-0390325 and 10-0423615, and use of reversed phase chromatography is described in Korean Patent Registration Nos. 10-0065197 and 10-0423615, Korean Patent Publication No. 10-2004-0065567 and Korean Patent Registration No. 10-0900033. Further, use of hydrophobic chromatography is described in Korean Patent Registration Nos. 10-0344059 and 10-0567448, and use of batch ion-exchange chromatography is described in Korean Patent Registration No. 10-0297927. Lastly, use of hydroxyapatite chromatography is described in Korean Patent Registration Nos. 10-0390325 and 10-0900013 and U.S. Pat. No. 7,619,073. Although the above-described techniques describe the purification of EPO, they do not describe purification of NESP having a lower isoelectric point than EPO.

Meanwhile, U.S. Pat. No. 7,217,689 disclosing NESP material describes use of anion exchange chromatography in the Examples.

WO2010/008823 A2 describes use of anion exchange or adsorption chromatography together with cation exchange chromatography for purification of NESP. In particular, this publication proposes a method for separating isoforms having more sialic acid residues through cation exchange chromatography.

As described, the purification method in the existing patents relating to EPO involves the use of columns inapplicable in industrial-scale production or the complicated purification processes of four or more steps. In addition, the method is not applicable for NESP having a lower isoelectric point owing to change in physicochemical properties due to the addition of sugar chains. The recently-disclosed sole patent relating to purification of NESP involves four steps, and its main process of separating isoforms having more sialic acid residues uses cation exchange chromatography. In contrast, anion exchange chromatography which is capable of more precisely separating the isoforms having more sialic acid residues is used in the present invention. Further, the present purification procedure is consisting of simpler three-step chromatographic processes, and it allows purification of erythropoietin analogs having a low isoelectric point faster at lower cost.

Throughout the specification, a number of publications and patent documents are referred to and cited. The disclosure of the cited publications and patent documents is incorporated herein by reference in its entirety to more clearly describe the state of the related art and the present disclosure.

DISCLOSURE

Technical Problem

The present inventors have made efforts to develop a method for purifying erythropoietin analogs with high purity having a lower isoelectric point than naturally occurring erythropoietin from culture solution of animal cells. As a result, we have developed a novel purification protocol for erythropoietin analogs (Darbepoetin alfa) having a low isoelectric point expressed in animal cells and demonstrated that the erythropoietin analogs having a low isoelectric point below 4 can be purified conveniently, quickly and effectively with high purity using the purification protocol.

Therefore, it is an object of this invention to provide a method for purifying an erythropoietin analog having an isoelectric point below 4 and a complicated sugar structure.

Other objects and advantages of the present invention will become apparent from the detailed description to follow taken in conjugation with the appended claims and drawings.

Technical Solution

In one aspect of this invention, there is provided a method for purifying an erythropoietin (EPO) analog having an isoelectric point below 4, comprising:

(a) Obtaining a pretreated solution by removing animal cells from a culture solution of the animal cells, wherein the animal cells express an erythropoietin analog having an isoelectric point below 4;

(b) Obtaining a first fraction comprising the erythropoietin analog by subjecting the pretreated solution to first ion exchange chromatography;

(c) Obtaining a second fraction comprising the erythropoietin analog by subjecting the first fraction to adsorption chromatography; and (d) Obtaining a third fraction comprising the erythropoietin analog by subjecting the second fraction to second ion exchange chromatography.

The present inventors have made efforts to develop a method for purifying erythropoietin analogs with high purity having a lower isoelectric point than naturally occurring erythropoietin from culture solution of animal cells. As a result, we have developed a novel purification protocol for erythropoietin analogs having a low isoelectric point expressed in animal cells and demonstrated that the erythropoietin analogs having a low isoelectric point below 4 can be purified conveniently, quickly and effectively with high purity using the purification protocol.

Each step of the present method for purifying an erythropoietin analog will be described in detail.

Step (a): Obtaining Pretreated Solution from Culture Solution of Animal Cells Expressing Erythropoietin Analog According to the present invention, first, a pretreated solution is obtained from a culture solution of animal cells expressing an erythropoietin analog having an isoelectric point below 4 by removing the animal cells from the culture solution.

The animal cells expressing an erythropoietin analog having an isoelectric point below 4 useful in the present invention include preferably mammalian, rodent, avian or insect cells, more preferably Chinese hamster ovary (CHO), VERO, HeLa, WI38, baby hamster kidney (BHK), COS or Madin-Darby canine kidney (MDCK) cells, further more preferably CHO, VERO, HeLa or MDCK cells, most referably CHO cells.

The erythropoietin analog having an isoelectric point below 4 comprises one or more mutation in the amino acid sequence of naturally occurring erythropoietin. The erythropoietin analog having a low isoelectric point can be prepared by mutagenesis such as addition, deletion or substitution of an amino acid residue. Through this, the sites of glycosylation may be increased or altered. The erythropoietin analog having a low isoelectric point has more carbohydrate chains than naturally occurring erythropoietin, and has at least one additional sugar chain. Although the erythropoietin analog having a low isoelectric point exhibits higher sialic acid content than naturally occurring erythropoietin owing to the additional sugar chain, the 2-dimensional or 3-dimensional structure of the protein which is important in its biological activity is not altered thereby.

Whereas naturally occurring erythropoietin having three N-linked sugar chains comprise up to 14 sialic acid residues, the erythropoietin analog having at least one additional N-linked sugar chain may comprise more sialic acid residues. Since sialic acid is a negatively-charged sugar acid, the erythropoietin analog having at least four N-linked sugar chains has an isoelectric point below 4 whereas the naturally occurring erythropoietin having three N-linked sugar chains has an isoelectric point of 4 or higher. Accordingly, the erythropoietin analog is relatively more difficult to prepare than the erythropoietin.

For example, the erythropoietin analog having an isoelectric point below 4 of the present invention is one in which at least one additional glycosylation site at one or more location selected from 30, 51, 57, 69, 88, 89, 136 and 138 positions of EPO sequence (e.g. GenBank sequence M11319). Most preferably, the erythropoietin analog having an isoelectric point below 4 is a novel erythropoiesis-stimulating protein (NESP) comprising A30N, H32T, P87V, W88N and P90T mutations.

The animal cells expressing the erythropoietin analog may be cultured according to various methods known in the art. For example, one of fed-batch culturing, repeated fed-batch culturing or continuous culturing known as the methods for culturing CHO cells may be employed. Most preferably, repeated fed-batch culturing may be employed.

The culture of animal cells needs to be pretreated since it usually comprises various constituents (impurities) such as proteins, saccharides, fats, etc.

As used herein, the term 'pretreatment' refers to a process of removing impurities prior to performing column chromatography in order to improve the purification efficiency of the purification method according to the present invention.

According to a preferred embodiment, in the pretreatment step (a), the animal cells are removed from the culture solution of animal cells by (i) filtration through a depth filter and a membrane filter followed by ultrafiltration or (ii) centrifugation followed by ultrafiltration.

The pretreatment using the depth filter may be performed according to various methods known in the art. The depth filter is used to remove particles larger than a predetermined size from the culture solution. Unlike the membrane filter, the depth filter removes the particles from the culture solution by capturing them in matrices. Typically, the depth filter comprises a fibrous medium such as cellulose, glass fiber or polypropylene. The pretreatment using the membrane filter may be performed according to various methods known in the art. For example, the pretreatment may be performed using various membranes having pores having a predetermined size.

A filtrate obtained by performing filtration through the depth filter and the membrane filter is subjected to ultrafiltration. The ultrafiltration is performed using an ultrafiltration membrane having an appropriate molecular weight cut-off (MWCO). For example, the ultrafiltration may be performed using an ultrafiltration membrane having a molecular weight cut-off of 5-30 kDa. The ultrafiltration may provide an effect of concentration as well as filtration.

Alternatively, the pretreatment may be performed by centrifuging the cell culture and then performing ultrafiltration. The centrifugation may be performed at 2000-5000 rpm.

Through this pretreatment step, the volume of the animal cell culture solution comprising the erythropoietin analog having an isoelectric point below 4 may be reduced, and load of the chromatographic column may be decreased by removing various impurities present in the culture solution.

Step (b): Obtaining First Fraction by First Ion Exchange Chromatography

The pretreated solution obtained from the pretreatment step is subjected to first anion exchange chromatography to obtain a first fraction comprising the erythropoietin analog.

The first anion exchange chromatography may be performed using various anion exchange chromatography techniques known in the art. More preferably, strongly basic anion exchange chromatography may be employed.

An anion-exchange resin useful in the present invention has positively-charged functional groups covalently bonded to the resin. Preferably, the positively-charged functional group of the anion-exchange resin is amine or amino, more preferably primary amine, secondary amine, tertiary amine or quaternary amine, most preferably quaternary amine. Examples of the positively-charged functional group of the anion-exchange resin include quaternary amine (e.g. trimethylaminomethyl and triethylaminoethyl), aminoethyl, diethylaminoethyl and p-aminobenzyl.

In the present invention, polystyrene, polyacrylate, cellulose, Sephacel, dextran, agarose or Toyopearl, preferably cellulose, dextran or agarose, most preferably agarose may be used as a support of the anion-exchange resin. In addition, in the present invention, Q Sepharose or DEAE Sepharose, preferably Q Sepharose may be used as an anion-exchange agent.

In the first anion exchange chromatography step of the present invention, any buffer having a buffering power may be used. For example, sodium acetate, sodium phosphate, glycine-HCl or Tris may be used.

Various buffers, in particular Tris, may be used as an equilibration buffer, and the pH may be 6-8, preferably 7.0-7.6. As a washing buffer, a buffer (preferably, acetate buffer) of pH below 4.0 may be used. More preferably, a buffer of pH 3.0-6.0, further more preferably 4.0-4.5, may be used.

Various buffers containing an adequate salt (preferably, sodium chloride) may be used as an elution buffer. Particularly, Tris may be used, and the pH may be 6-8, preferably 7.0-7.6.

The pH and/or ionic strength appropriate for eluting the erythropoietin analog having an isoelectric point below 4 from a strongly basic anion-exchange agent may be determined empirically and may vary depending on various factors (e.g. the kind of the strongly basic anion-exchange agent, temperature, etc.). The ionic strength of the elution buffer may be provided by various salts. For example, sodium chloride may be used to provide the ionic strength.

Referring to Examples of this invention, the step (b) may be described as follows: A column (BPG 100/500, GE Healthcare) packed with 800 mL of Q Sepharose FF resin (GE Healthcare), which is a kind of strongly basic anion-exchange resin, is equilibrated using an equilibration buffer (e.g. 10 mM Tris buffer, pH 7.4). Then, the pretreated solution obtained in the step (a) is added to the Q Sepharose column and impurities are removed by washing, so that most of the substance bound to the resin is the erythropoietin analog having an isoelectric point below 4. According to a preferred embodiment, 100 mM acetate buffer (pH 4.0) is used as a washing buffer. The erythropoietin analog having an isoelectric point below 4 may be eluted using Tris buffer containing sodium chloride. The concentration of sodium chloride may be preferably 50-500 mM, more preferably 100-400 mM, most preferably 200-300 mM.

In the step (b), the pretreated solution obtained in the step (a) is subjected to first ion exchange chromatography to obtain the first fraction comprising the erythropoietin analog.

Step (c): Obtaining Second Fraction by Adsorption Chromatography

The first fraction obtained from the first ion exchange chromatography step is subjected to adsorption chromatography to obtain a second fraction comprising the erythropoietin analog.

During the adsorption chromatography, separation of the sample occurs between a mobile phase which is liquid and a stationary phase (adsorbent resin) which is solid owing to the difference in adsorptivity.

The stationary phase that can be used in the adsorption chromatography of the present invention includes preferably silica, alumina, magnesium oxide and calcium phosphate (preferably, hydroxyapatite), but is not limited thereto. More preferably, the stationary phase may be calcium phosphate, most preferably hydroxyapatite. Hydroxyapatite has excellent resolving and separating power. Where hydroxyapatite is used as the stationary phase, phosphate buffer may be used as the mobile phase.

Where hydroxyapatite is used, phosphate buffer may be used as an equilibration buffer, and the pH may be 6-8, preferably 6.0-7.0. Phosphate buffer comprising an appropriate salt (preferably, sodium chloride) may be used as an elution buffer, and the pH may be 6-8, specifically 6.0-7.0.

Referring to Examples of this invention, the step (c) may be described as follows: A column packed with hydroxyapatite resin (type I or II, 20-40 μm) is equilibrated using an equilibration buffer (e.g. 20 mM phosphate buffer, pH 6.0-7.0). Then, the first fraction obtained in the step (b) is added to the hydroxyapatite column and the erythropoietin analog having an isoelectric point below 4 not adsorbed to the resin is obtained as an unadsorbed fraction. Protein impurities adsorbed to the hydroxyapatite resin may be eluted using an elution buffer (e.g. 500 mM phosphate buffer, pH 6.0-7.0).

Step (d): Obtaining Third Fraction by Second Ion Exchange Chromatography

The second fraction obtained from the adsorption chromatography step is subjected to second anion exchange chromatography to obtain a third fraction comprising the erythropoietin analog.

The second anion exchange chromatography may be performed using various anion exchange chromatography techniques known in the art. Preferably, strongly basic anion exchange chromatography may be employed.

An anion-exchange resin in the present invention may have positively-charged functional groups. Preferably, the positively-charged functional group of the anion-exchange resin is amine or amino, more preferably primary amine, secondary amine, tertiary amine or quaternary amine, most preferably quaternary amine.

In the present invention, polystyrene, polyacrylate, polystyrene/divinylbenzene, cellulose, Sephacel, dextran, agarose or Toyopearl, preferably agarose or polystyrene/divinylbenzene, may be used as a support of the anion-exchange resin.

In the present invention, Q Sepharose, DEAE Sepharose, SOURCE 15Q, SOURCE 30Q, Capto DEAE or Capto Q, preferably SOURCE 15 Q or SOURCE 30 Q, may be used as an anion-exchange agent.

In the second anion exchange chromatography step of the present invention, any buffer having a buffering power may be used. For example, sodium acetate, sodium phosphate, glycine-HCl or Tris may be used.

Various buffers, in particular acetate buffer, may be used as an equilibration buffer, and the pH may be 3-6, preferably 4-5. As a washing buffer, a buffer (preferably, glycine buffer) of pH 2.0-4.0, more preferably 3.0-4.0, may be used. Various buffers, particularly phosphate buffer, containing an adequate salt (preferably, sodium chloride) may be used as an elution buffer, and the pH may be 6-8, preferably 7.0-7.6. The concentration of the salt, particularly sodium chloride, contained in the elution buffer may be preferably 100-500 mM.

Referring to Examples of this invention, the step (d) may be described as follows: A column (XK 50/30, GE Healthcare) packed with 800 mL of Q Sepharose SOURCE 15Q or 30Q resin (GE Healthcare), which is a kind of strongly basic anion-exchange resin, is equilibrated using an equilibration buffer (e.g. 20 mM phosphate buffer, pH 6.0-7.0). Then, the second fraction comprising the erythropoietin analog obtained from the adsorption chromatography step is added to the SOURCE 15Q or 30Q column, and the resin is washed using a first washing buffer (e.g. 20 mM acetate buffer, pH 4.0-5.0) and a second washing buffer (e.g. 20 mM glycine buffer, pH 2.2-2.4).

According to a preferred embodiment, the step (c) and the step (d) are performed as a single process. Since the second fraction requires no treatment prior to the step (d), the columns of the step (c) and the step (d) may be connected directly. In this case, the time spent for the step (c) and the step (d) may be reduced and the second fraction and the third fraction may be obtained in short time.

According to the present invention, protein isoforms excluding the erythropoietin analog having an isoelectric point below 4 can be removed effectively in the step (d). Since the small amount of protein impurities not adsorbed in the step (c) are effectively removed in the step (d), the fraction containing the erythropoietin analog having an isoelectric point below 4 can be obtained with high purity.

The present method is very effective for the purification of the erythropoietin analog having an isoelectric point below 4, preferably an erythropoiesis-stimulating factor having four or more N-linked sugar chains, most preferably an NESP.

Advantageous Effects

The features and advantages of the present invention are summarized as follows:

(a) The present invention provides a novel method for purifying erythropoietin (EPO) analogs having an isoelectric point below 4.

(b) Whereas naturally occurring EPO having three N-linked sugar chains comprises up to 14 sialic acid residues, the erythropoietin analog having four or more N-linked sugar chain may comprise more sialic acid residues. The erythropoietin analog having four or more N-linked sugar chains has an isoelectric point below 4 whereas the naturally occurring erythropoietin having three N-linked sugar chains has an isoelectric point of 4 or higher. Accordingly, the erythropoietin analog is relatively more difficult to prepare then the erythropoietin. Difficulties of producing the erythropoietin analog having a low isoelectric point caused by its physicochemical properties is solved in the present invention. Therefore, the present invention provides a method enabling production of the erythropoietin analog having a low isoelectric point in industrial scale.

(c) The present invention provides a purification method, whereby protein impurities can be effectively removed via three chromatography steps and the erythropoietin analog can be obtained with high purity.

(d) Since the adsorption chromatography and the second ion exchange chromatography steps of the present purification method can be performed as a single process, the time required for the purification can be reduced.

DESCRIPTION OF DRAWINGS

Lane 1: molecular weight standard (Bio-Rad)
Lane 2: culture solution of animal cells (ultrafiltration filtrate)
Lane 3: first fraction obtained from first ion exchange chromatography
Lane 4: second fraction obtained from adsorption chromatography
Lane 5: third fraction obtained from second ion exchange chromatography
Lane 6: standard NESP

Lane 1: fraction subjected to second ion exchange chromatography
Lane 2: pH washing purified fraction obtained from second ion exchange chromatography
Lane 3: purified fraction obtained from second ion exchange chromatography
Lane 4: standard NESP

Lane 1: standard NESP
Lane 2: Purified fraction obtained from second ion exchange chromatography FIGS. 9a-9d shows size exclusive chromatograms showing purity of fractions obtained from each step of the present purification method.

Mode for Invention

Hereinafter, the present invention will now be described in further detail by examples. It would be obvious to those skilled in the art that these examples are intended to be more concretely illustrative and the scope of the present invention as set forth in the appended claims is not limited to or by the examples.

EXAMPLES

Example 1

Culturing of Cells Producing Erythropoietin Analogs

CHO cells producing a glycoprotein with five amino acids (A30N, H32T, P87V, W88N and P90T) of EPO substituted were cultured in a 50-L container. The cells were cultured by repeated fed-batch culturing, which is one of the methods for culturing CHO cells well known in the art. A chemically defined medium or a serum-free medium such as the SFM4CHO medium available from HyClone was used. The culture solution was recovered after a production phase of about 5 days. The cell concentration was $8 \times 10^6$ cells/mL or higher and the cell viability was at least 95%.

Example 2

Microfiltration and Ultrafiltration

The cells and cell debris were removed from the culture solution of animal cells obtained in Example 1 using a depth filter (Millipore) and a membrane filter (Sartorius, 0.2 μm), respectively. Subsequently, the resulting microfiltration filtrate was passed through an ultrafiltration membrane (Millipore, MWCO: 5-30 kDa) in order to remove salts and saccharides smaller than 5-30 kDa. Diafiltration and concentration were performed using Tris buffer having volume of 10 times than initially concentrated volume.

Example 3

First Anion Exchange Chromatography

Figure 1:
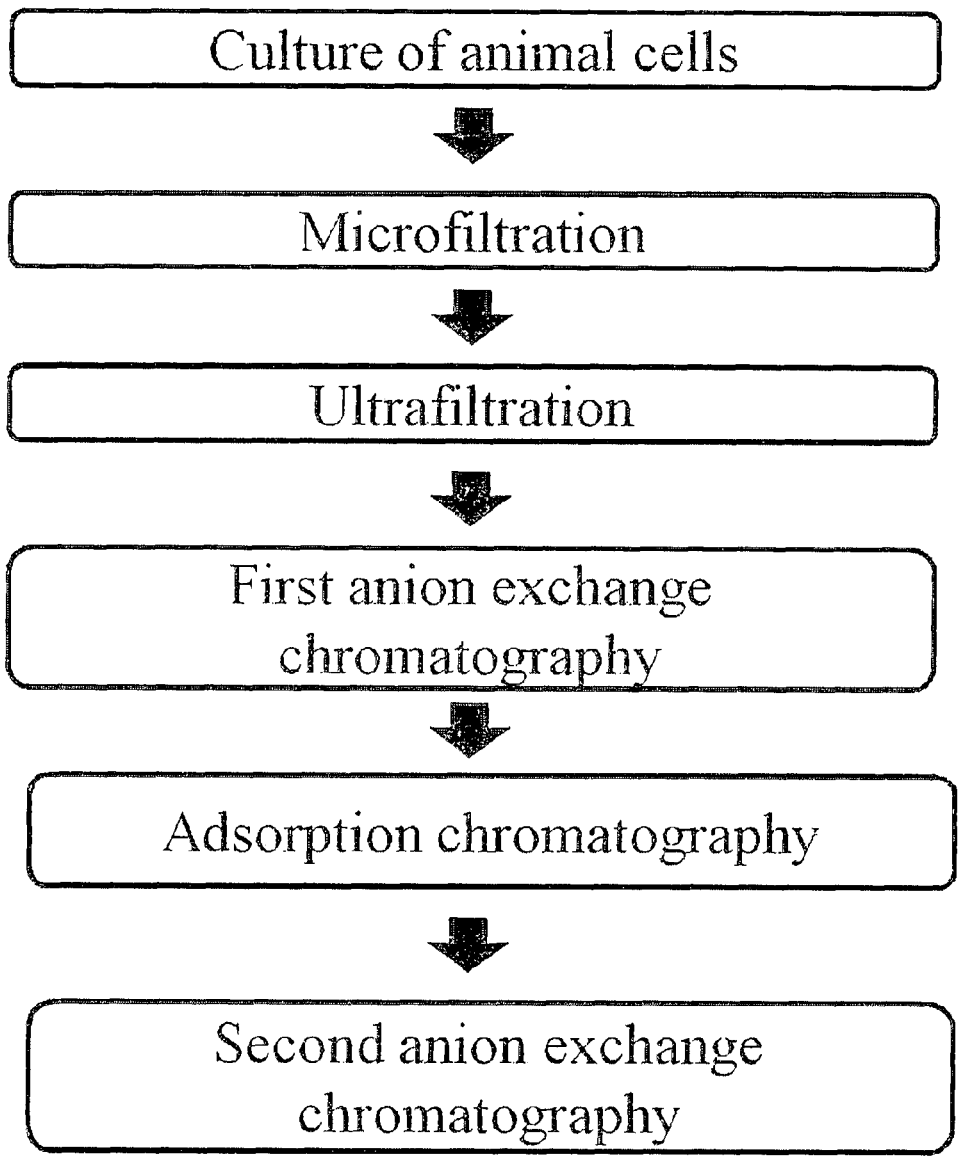
FIG. 1 briefly illustrates a preferred method for purifying an erythropoietin analog having an isoelectric point below 4 from a culture solution of animal cells according to the present invention.
Figure 2:
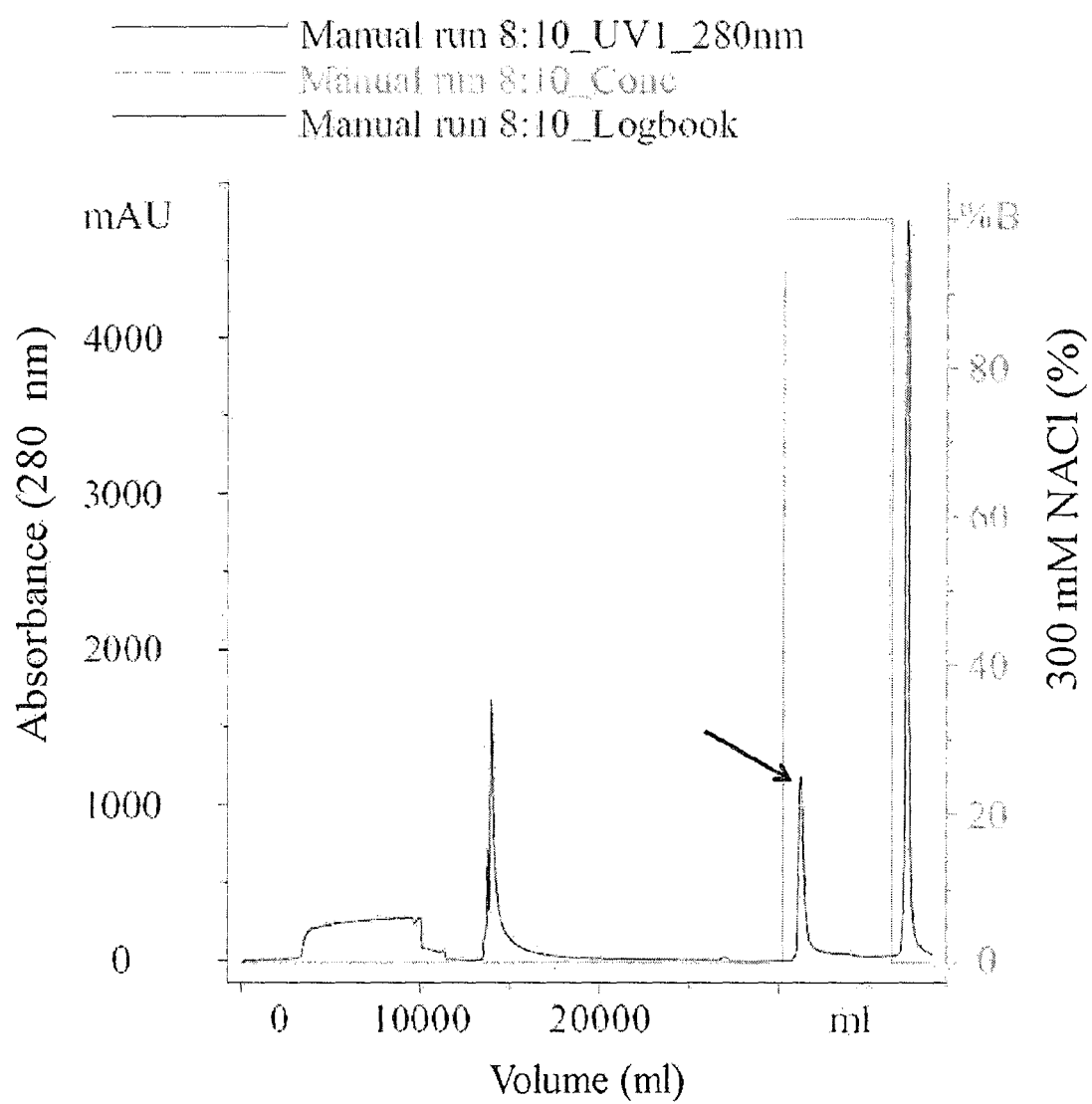
FIG. 2 shows a chromatogram of a first fraction comprising an erythropoietin analog having an isoelectric point below 4 obtained by first ion exchange chromatography in a purification method according to the present invention. The arrow indicates the chromatogram peak of the target protein.

Anion exchange chromatography was performed using the AKTApilot system (GE, USA), and a BPG 100/500 column (GE) packed with 800 mL of Q Sepharose FF resin (GE) was used. The column was equilibrated using 10 mM Tris buffer of pH 7.4 at a flow rate of 300 mL/min. The column was washed using 100 mM acetate buffer of pH 4.0 as a washing buffer, and the protein adsorbed to the Q Sepharose FF gel was eluted using an equilibration buffer containing 300 mM sodium chloride. The resulting first anion exchange chromatogram is shown in FIG. 2.

Example 4

Adsorption Chromatography

Figure 3:
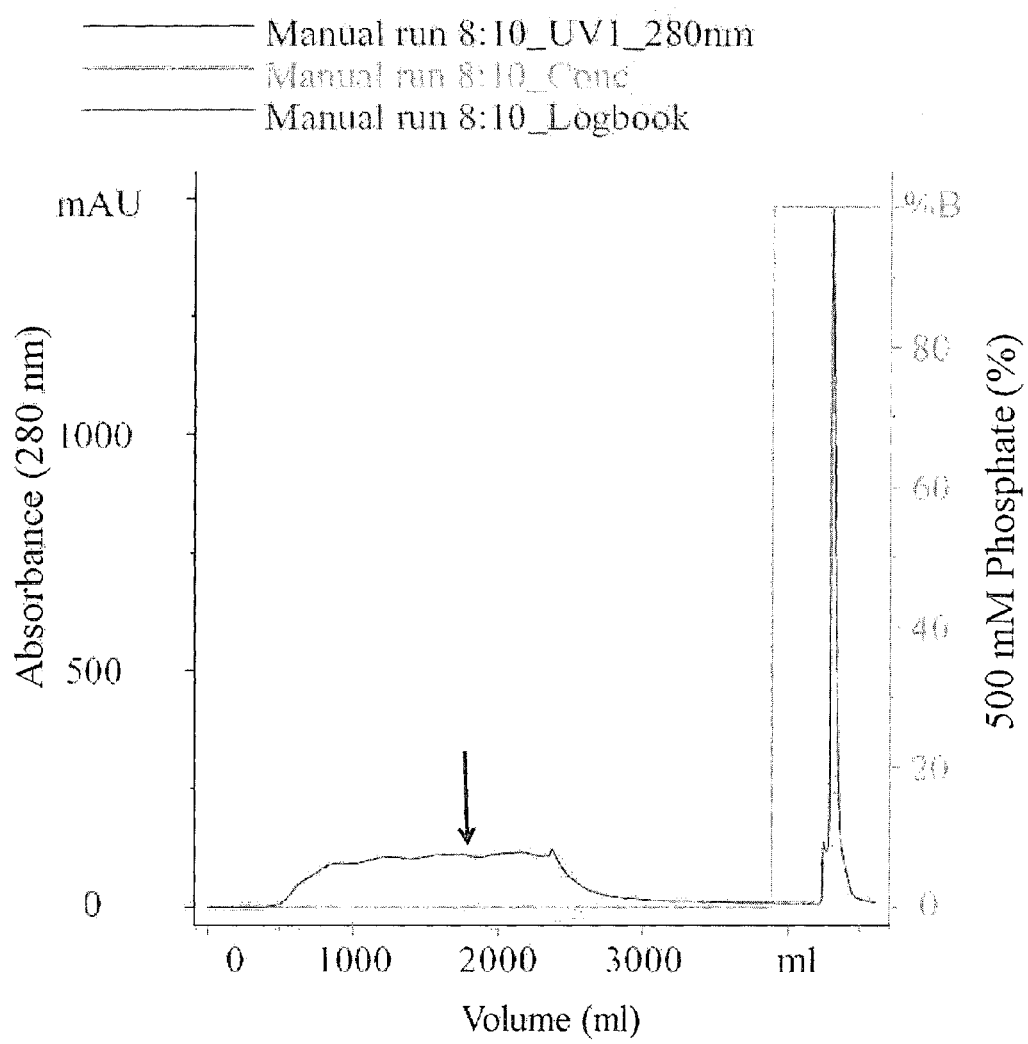
FIG. 3 shows a chromatogram of a second fraction comprising an erythropoietin analog having an isoelectric point below 4 obtained by adsorption chromatography in a purification method according to the present invention. The arrow indicates the chromatogram peak of the target protein.

Adsorption chromatography was performed using the AKTApurifier system, and an XK 50/30 column packed with 430 mL of hydroxyapatite type I or II resin (20-40 μm, Bio-Rad) was used. The column was equilibrated using 20 mM phosphate buffer of pH 6.0-7.0 at a flow rate of 20 mL/min. The fraction obtained from the first anion exchange chromatography was passed through the column, whereby the erythropoietin analog was recovered as an unadsorbed fraction. The column was then washed using 500 mM phosphate buffer of pH 6.0-7.0 as a washing buffer to remove the protein impurities remaining in the column. For efficient second ion exchange chromatography, ultrafiltration (MWCO 5-30 kDa) was performed before performing the adsorption chromatography. The resulting adsorption chromatogram is shown in FIG. 3.

Example 5

Second Anion Exchange Chromatography

Figure 4:
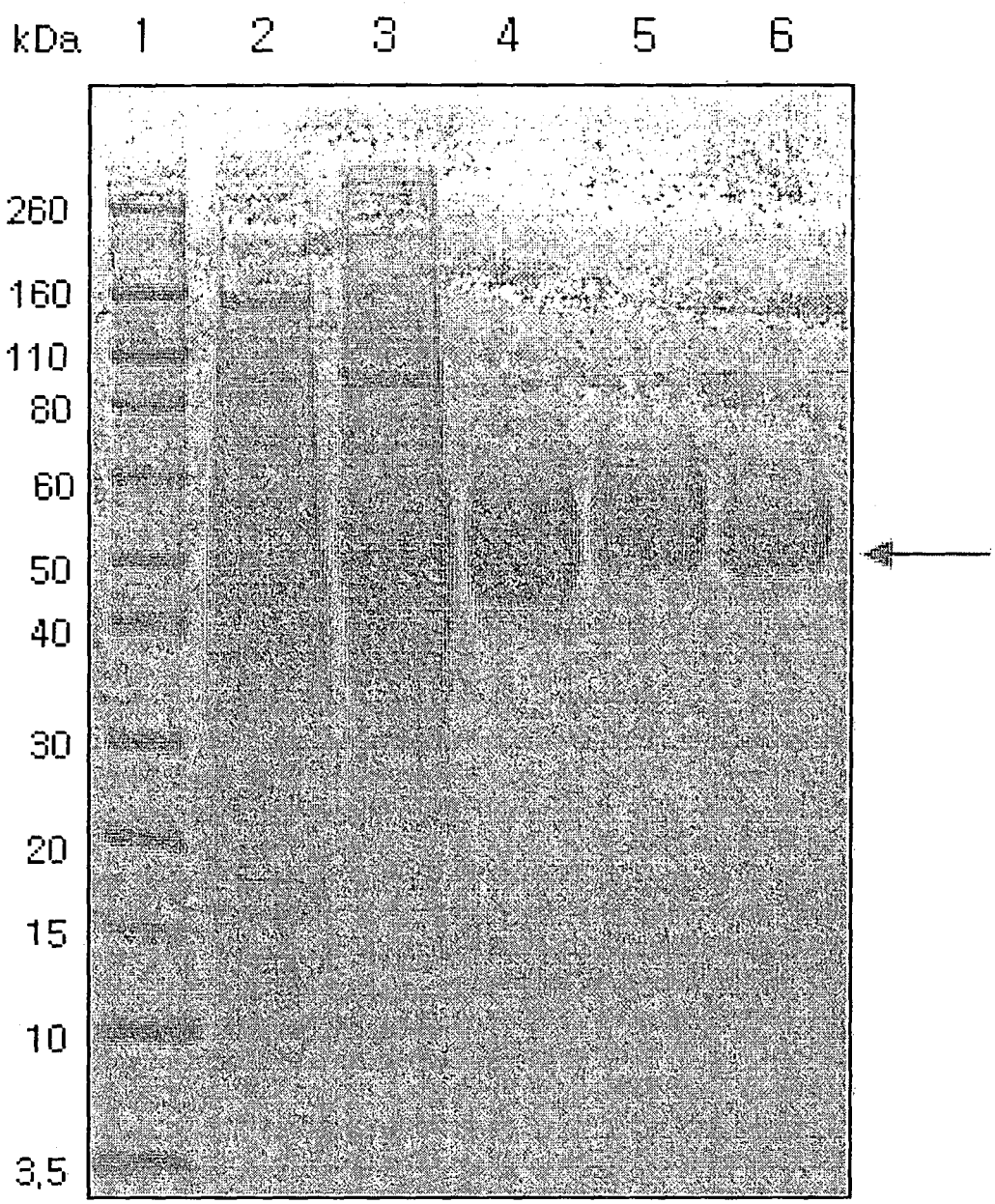
FIG. 4 shows a result of sodium dodecyl sulfate polyacrylamide gel electrophoresis and Coomassie staining of fractions obtained by a purification method according to the present invention. The arrow indicates the bands of the target protein and a standard NESP.
Figure 5:
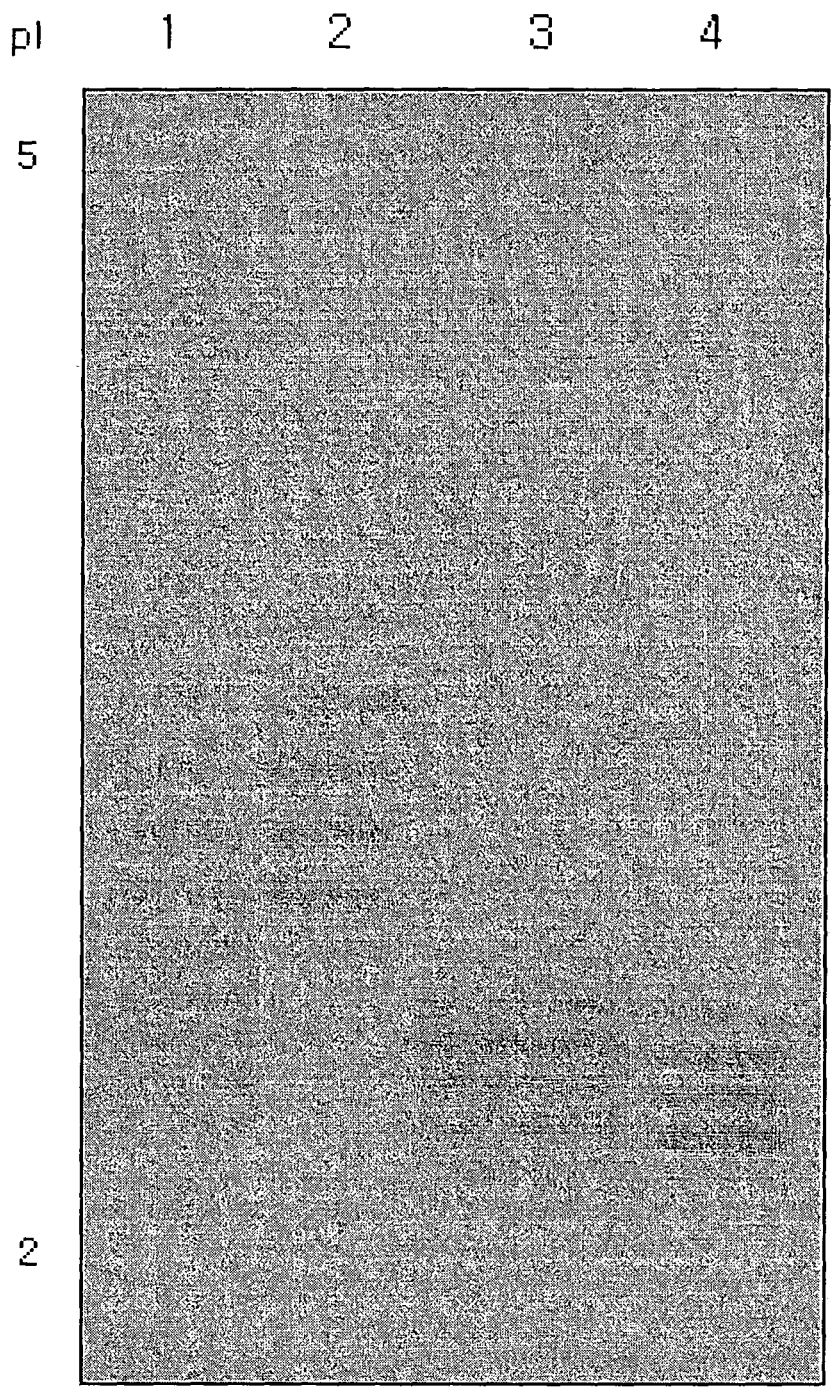
FIG. 5 shows a result of isoelectric focusing and Coomassie staining of a third fraction obtained in the final step of a purification method according to the present invention.
Figure 6:
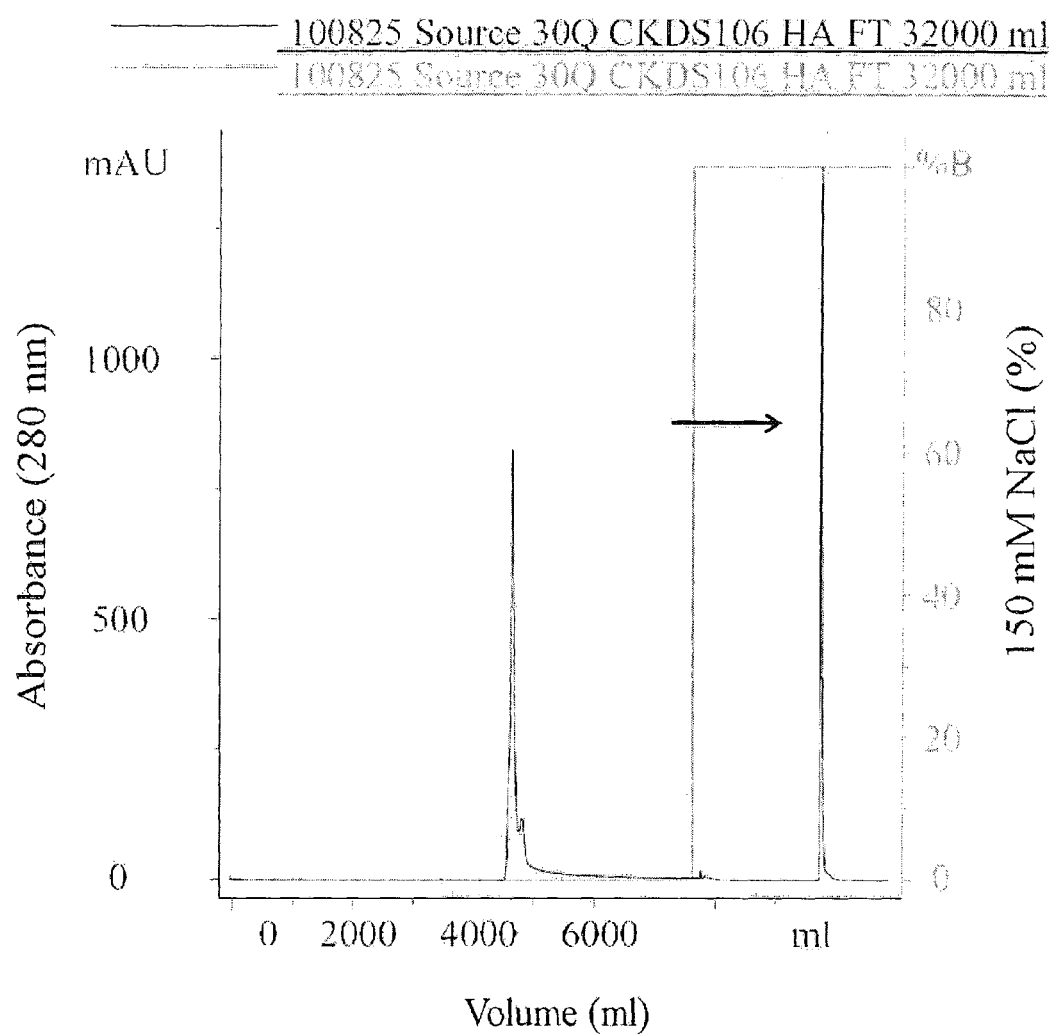
FIG. 6 shows a chromatogram of a third fraction comprising an erythropoietin analog having an isoelectric point below 4 obtained by second anion exchange chromatography in a purification method according to the present invention. The arrow indicates the chromatogram peak of the target protein.
Figure 7:
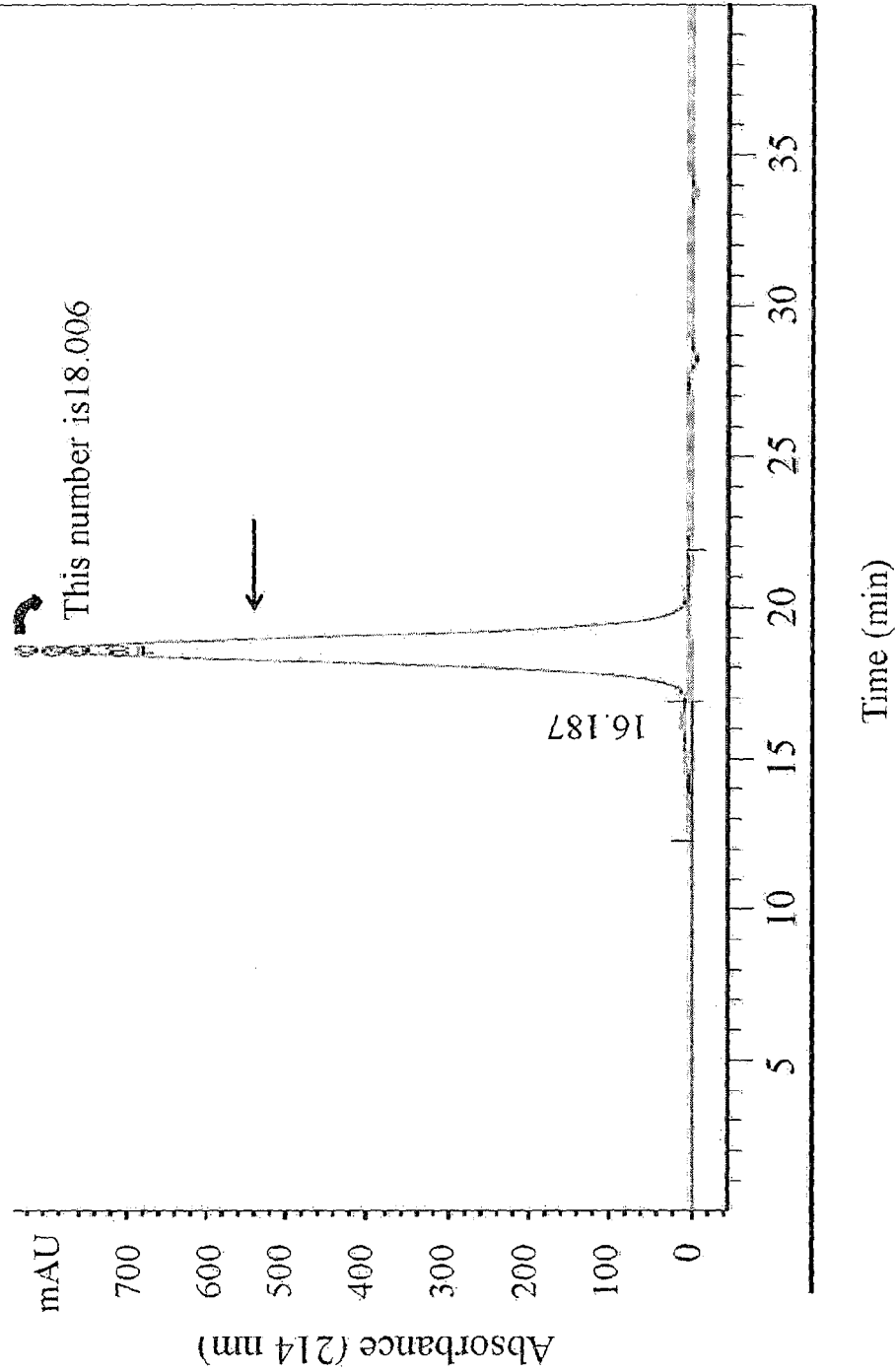
FIG. 7 shows a chromatogram of NESP obtained by size exclusion chromatography in a purification method according to the present invention. The arrow indicates the chromatogram peak of the target protein.

Second anion exchange chromatography was performed using the AKTApurifier system, and an XK 50/30 column packed with 200 mL of SOURCE 15Q or 30Q resin (GE) was used. The column was equilibrated using 20 mM acetate buffer of pH 4.0-5.0 at a flow rate of 25 mL/min. The column was washed using 20 mM glycine buffer of pH 2.2-2.4 as a washing buffer, and the protein adsorbed to the SOURCE 15Q or 30Q gel was eluted using phosphate buffer containing 100-500 mM sodium chloride. With respect to each fractions, the presence of impurities (FIG. 4) and the isoform of the erythropoietin analog (FIG. 5) were analyzed by sodium dodecyl sulfate polyacrylamide gel electrophoresis and Coomassie staining, and by isoelectric focusing and Coomassie staining. It was demonstrated that the final fraction showed a similar protein band pattern with the standard NESP in the isoform analysis. The resulting second anion exchange chromatogram is shown in FIG. 6. In addition, the purity of purified proteins obtained from the second anion exchange chromatogram was analyzed by size exclusion chromatography. The purity was at least 98% as shown in FIG. 7.

Example 6

Simultaneous Performance of Adsorption Chromatography and Second Ion Exchange Chromatography Adsorption chromatography and second anion exchange chromatography were performed simultaneously using the AKTApurifier system. An XK 50/30 column (GE) packed with 430 mL of hydroxyapatite resin and an XK 50/30 column (GE) packed with 200 mL of SOURCE 15Q or 30Q resin were connected via a connector, and the columns were equilibrated using 20 mM phosphate buffer of pH 6.0-7.0

Figure 8:
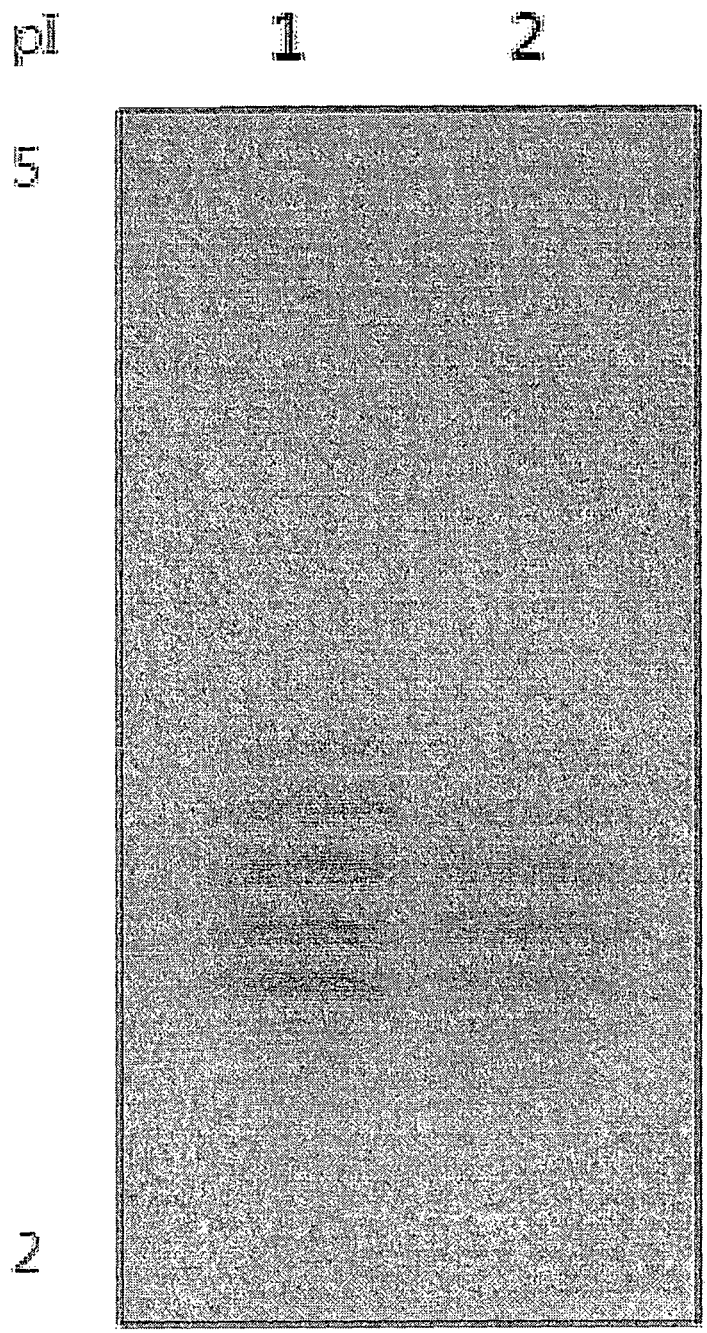
FIG. 8 shows a result of isoelectric focusing and Coomassie staining of a fraction obtained by adsorption chromatography and second ion exchange chromatography in a purification method according to the present invention.
Figure 9A:
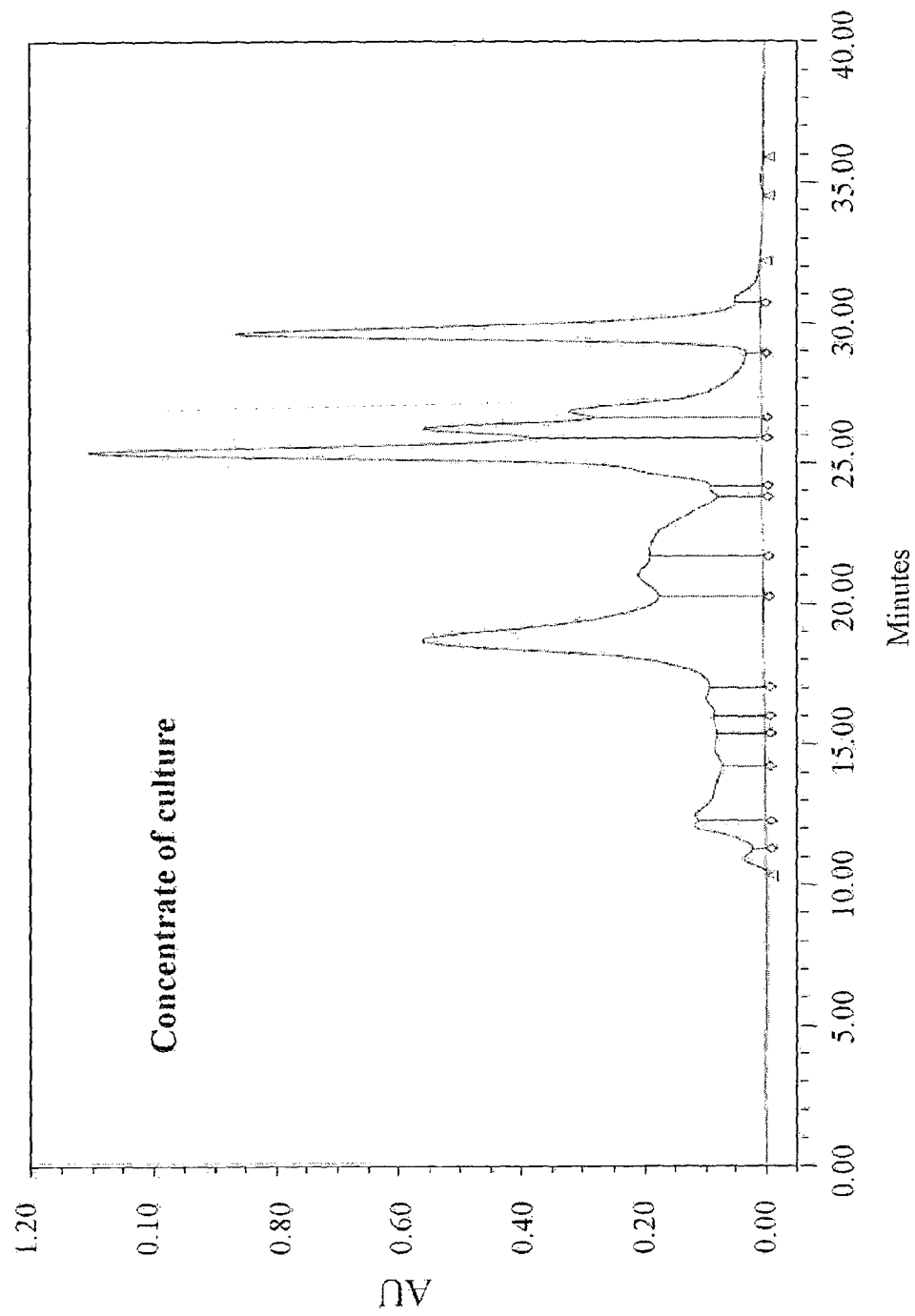
Figure 9C:
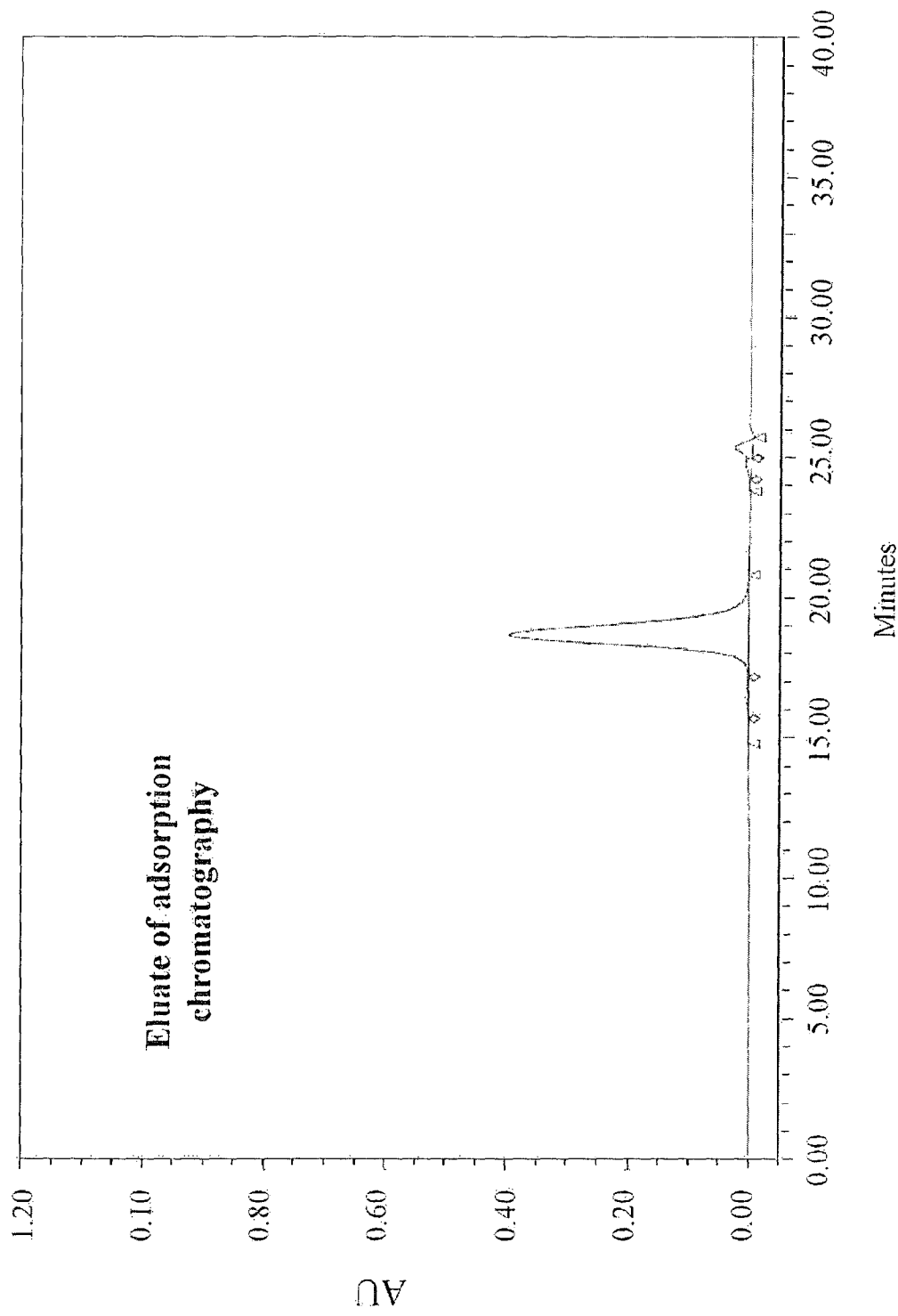
Figure 9D:
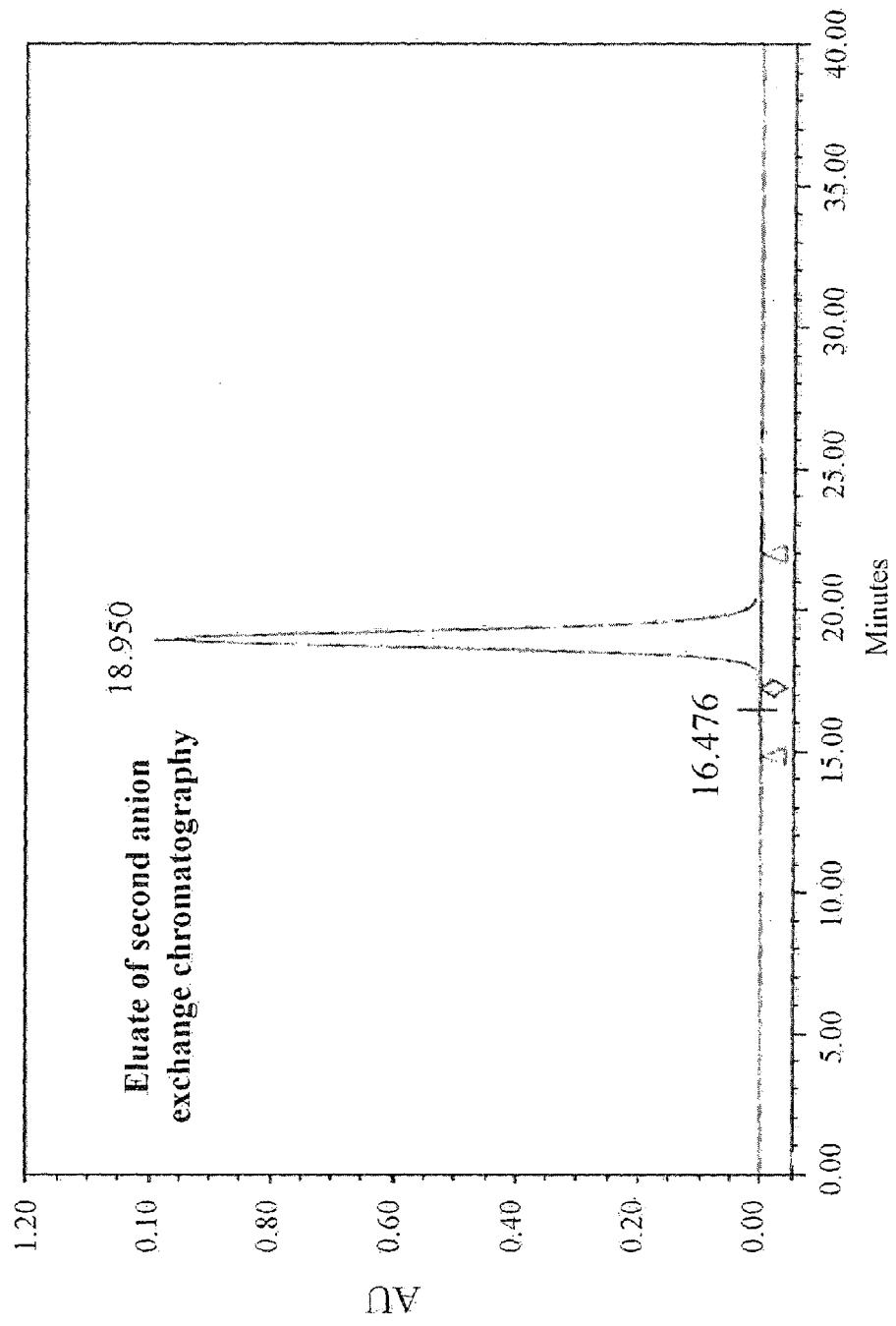

(equilibration buffer) at a flow rate of 20 mL/min. Then, the fraction obtained from the first anion exchange chromatography was passed through an ultrafiltration membrane (MWCO: 5-30 kDa) and the resulting filtrate was added to the column connected thereto. Then, protein impurities not adsorbed to the column were removed by injecting an equilibration buffer at a flow rate of 20 mL/min. After the washing, the hydroxyapatite column was removed and only the SOURCE column was mounted on the AKTApurifier system. Then, the target protein was eluted in the same manner as described in Example 5. The isoform of the final purification product was analyzed by isoelectric focusing and Coomassie staining (FIG. 8). As a result, it was demonstrated that there was no difference in the purity of the final product between the method wherein the adsorption chromatography and the second ion exchange chromatography were performed independently and one wherein the adsorption chromatography and the second ion exchange chromatography were performed sequentially as a single process. Further, it was demonstrated that the final fraction showed a similar protein band pattern as the standard NESP.

Example 7

Analysis for Fractions from Each Step

Each fraction and molecular weight standard were electrophoresed on 4-12% gradient sodium dodecyl sulfate polyacrylamide gel (SDS-PAGE) for 1 hour under a constant voltage of 150 V. Following the electrophoreses, the gel was stained for 30 minutes with Coomassie stain.

10 µg of each fraction was electrophoresed on 2-5% isoelectric focusing (IEF) gel for each 1 hour under four constant voltage steps of 100 V, 200 V, 400 V and 550 V. Following the electrophoreses, the gel was stained for 30 minutes with Coomassie stain.

Example 8

Establishment of Pilot-scale Purification Process

A pilot-scale purification process was established using the purification method of the present invention. The yield of each purification step and the final yield are given in Table 1. It was demonstrated that high yield could be achieved although the isoforms having a high isoelectric point were removed to improve purity and quality as medicine.

become apparent to those skilled in this art, and the scope of this invention is to be determined by appended claims and their equivalents.

The invention claimed is:

1. A method for purifying an erythropoietin (EPO) analog having an isoelectric point below 4, which analog is darbepoetin alfa, comprising
    obtaining a pretreated solution by removing animal cells from a culture solution of the animal cells, wherein the animal cells express the erythropoietin analog having an isoelectric point below 4; and, as the sole three chromatography steps of the method:
    (a) Obtaining a first fraction comprising the erythropoietin analog by subjecting the pretreated solution to first anion exchange chromatography;
    (b) Obtaining a second fraction comprising the erythropoietin analog by subjecting the first fraction to hydroxyapatite chromatography, whereby the second fraction is obtained as an unabsorbed fraction; and
    (c) Obtaining a third fraction comprising the erythropoietin analog by subjecting the second fraction to second anion exchange chromatography.

2. The method according to claim 1, wherein the animal cells expressing the erythropoietin analog comprise Chinese hamster ovary (CHO), VERO, HeLa, W138, baby hamster kidney (BHK), COS or Madin-Darby canine kidney (MDCK) cells.

3. The method of according to claim 1, wherein the obtaining of the pretreated solution is performed by (i) filtration through a depth filter and a membrane filter followed by ultrafiltration or (ii) centrifugation followed by ultrafiltration.

4. The method according to claim 1, wherein a buffer of pH below 4.0 is used as a washing buffer in the first anion exchange chromatography of the step (a).

5. The method according to claim 1, wherein a buffer of pH 2.0-4.0 is used as a washing buffer in the second anion exchange chromatography of the step (c).

6. The method according to claim 5, wherein the buffer contains glycine with a pH 2-3.

7. The method according to claim 6, wherein the buffer contains glycine with a pH 2.2-2.4.

TABLE 1

| Purification step | Volume (mL) | Concentration (mg/mL) | Protein content (mg) | Purity (%) | Content (mg) | Overall yield (%) |
|---|---|---|---|---|---|---|
| Concentrate of culture | 6780 | 0.5 | 3390.0 | 22.4 | 759.4 | — |
| First anion chromatography | 2466 | 0.3 | 813.8 | 60.1 | 489.1 | 60.1 |
| Adsorption chromatography | 4695 | 0.1 | 469.5 | 94.0 | 441.3 | 54.2 |
| Second anion chromatography | 424 | 0.4 | 148.4 | 99.0 | 146.9 | 18.1 |

Having described a preferred embodiment of the present invention, it is to be understood that variants and modifications thereof falling within the spirit of the invention may 8. The method according to claim 1, wherein the step (b) and the step (c) are performed as a single process.

* * * * *